United States Patent [19]

Bull

[11] 4,436,667

[45] Mar. 13, 1984

[54] PROCESS FOR PREPARING CYCLOPROPANE CARBOXYLIC ACID ESTER DERIVATIVES

[75] Inventor: Michael J. Bull, Kent, England

[73] Assignee: Shell Internationale Research Maatschappij B. V., The Hague, Netherlands

[21] Appl. No.: 252,892

[22] Filed: Apr. 10, 1981

[30] Foreign Application Priority Data

Apr. 23, 1980 [GB] United Kingdom ................. 8013309

[51] Int. Cl.$^3$ .......................................... C07C 121/75
[52] U.S. Cl. ............................................. 260/465 D
[58] Field of Search ................................... 260/465 D

[56] References Cited

U.S. PATENT DOCUMENTS

| | | | |
|---|---|---|---|
| 4,024,163 | 5/1977 | Elliott et al. | 260/347.4 |
| 4,133,826 | 1/1979 | Warnant et al. | 260/465 D |
| 4,136,195 | 1/1979 | Warnant et al. | 424/304 |
| 4,151,195 | 4/1979 | Warnant et al. | 260/465 D |
| 4,176,195 | 11/1979 | Stoutamire | 424/304 |
| 4,260,633 | 4/1981 | Anderson et al. | 260/465 D |
| 4,261,921 | 4/1981 | Smeltz | 424/304 |

FOREIGN PATENT DOCUMENTS 2375161 7/1978 France .
1413491 11/1975 United Kingdom .

OTHER PUBLICATIONS

M. Elliott, et al., "Synthetic Insecticide With a New Order of Activity", Nature, vol. 248, pp. 710–711, Apr. 19, 1974.
Itaya, et al., "Synthetic Pyrethroids", A.C.S. Symposium Series 42, pp. 45–54(1977).

*Primary Examiner*—Ethel G. Love

*Attorney, Agent, or Firm*—Pravel, Gambrell, Hewitt, Kirk & Kimball

[57] ABSTRACT

This invention relates to the preparation of cyclopropane carboxylic acid ester derivatives, which are useful as pesticides.

There is provided a process for preparing a mixture of cis-isomers of a compound of formula

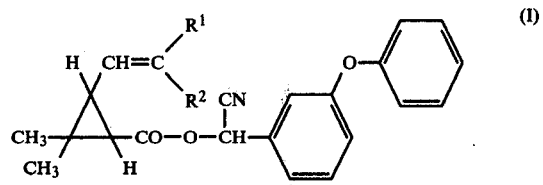

wherein $R^1$ and $R^2$ are independently selected from chlorine, bromine and methyl, consisting predominantly of the 1R cis S- and 1S cis R- isomers, which process comprises dissolving a mixture of 1S cis S- and 1R cis R- isomers of the compound of formula I, alone or in the presence of 1R cis S- and 1S cis R-isomers, in an organic amine base containing from 5 to 7 carbon atoms and being a secondary amine containing two branched alkyl groups or a tertiary amine, crystallizing out from a resulting solution of cis- isomers of formula I in the organic amine base a 1:1 mixture of the 1R cis S- and 1S cis R- isomers, and evaporating off the organic amine base.

The process of the invention yields a product which may contain up to twice as much of the most active isomer of the compound of formula I as a recemic mixture of all four cis-isomers, and is a readily effected process which does not involve any sterospecific synthesis or optical resolution steps.

11 Claims, No Drawings

PROCESS FOR PREPARING CYCLOPROPANE CARBOXYLIC ACID ESTER DERIVATIVES

This invention relates to the preparation of pesticidal cyclopropane carboxylic acid ester derivatives.

Cyclopropane carboxylic acid ester derivatives of general formula

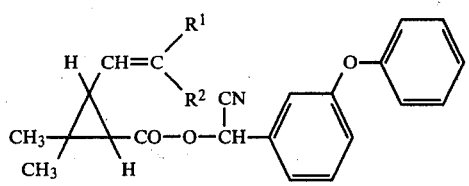

wherein $R^1$ and $R^2$ are independently selected from chlorine, bromine and methyl, are known compounds having pesticidal activity, see for example U.K. Pat. No. 1,413,491 or U.S. Pat. No. 4,024,163. These derivatives are members of a class of pesticidal compounds commonly referred to in the art as "pyrethroid insecticides". Compounds of formula I contain two centres of asymmetry in the cyclopropane ring of the acid moiety and a third centre of asymmetry in the alcohol moiety, leading to the existence of eight possible isomers. In general, superior pesticidal activity resides among the compounds having cis-configuration about the cyclopropane ring, as disclosed by Itaya et al in "Synthetic Pyrethroids", ACS Symposium Series 42, Pages 45 to 54, and the isomer which has the greatest pesticidal activity is generally that isomer which is conveniently designated the 1R cis S-isomer, 1R cis-designating configuration in the acid moiety and S-designating configuration in the alcohol moiety, as described in Elliott et al in Nature, Vol. 248, Pages 710 and 711 (1974).

Attempts to produce 1R cis S-single isomers rest either on synthesis routes which inherently produce intermediates containing the cyclopropane carboxylic acid moiety in exclusively 1R cis-configuaration or on a route which involves an optical resolution step to separate 1R cis-compounds from 1S cis-compounds. Esterification of a 1R cis-intermediate to produce a derivative of formula I above leads to production of a mixture of 1R cis R- and 1R cis S-end products. Separation of these end products is possible by physical methods, at least in theory, since the 1R cis R- and 1R cis S-compounds are not enantiomers. However, although such preparation of 1R cis R and 1R cis S-compounds has proved to be relatively readily attainable when $R^1$ and $R^2$ are both bromine atoms, it has proved to be more difficult and more costly in other cases, for example when $R^1$ and $R^2$ are both chlorine atoms.

The Applicants have now discovered a surprisingly simple and inexpensive method of increasing the 1R cis S-isomer content of a mixture of cis-isomers of formula I.

According to the invention there is provided a process for preparing a mixture of cis-isomers of a compound of formula

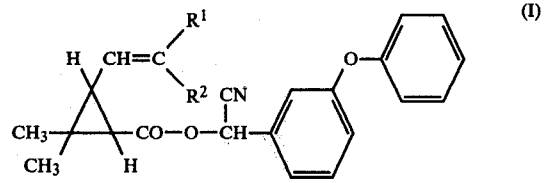

wherein $R^1$ and $R^2$ are independently selected from chlorine, bromine and methyl, consisting predominantly of the 1R cis- S- and 1S cis R-isomers, which process comprises dissolving a mixture of 1S cis S- and 1R cis R-isomers of the compound of formula I, alone or in the presence of 1R cis S- and 1S cis R-isomers, in an organic amine base containing from 5 to 7 atoms and being a secondary amine containing two branched alkyl groups or a tertiary amine, crystallising out from a resulting solution of cis-isomers of formula I in the organic amine base of 1:1 mixture of the 1R cis S- and 1S cis R-isomers, and evaporating off the organic amine base.

It is preferred that $R^1$ and $R^2$ are both chlorine or bromine atoms, and they are preferably both chlorine atoms.

The organic base causes racemisation to take place at the α-carbon atom of the alcohol moiety of the compound of formula I, so that the mixture of cis-isomers of formula I in solution in the organic base tends to become a racemic solution of all four cis-isomers, i.e. a solution containing equal quantities of 1R cis S-, 1S cis S-, 1R cis R- and 1S cis R-isomers, assuming that the initial mixture was optically inactive. However, the organic amine bases which are suitable for use in the process of the invention have the further property of being solvents in which the 1R cis S-/1S cis R-enantiomer pair of the isomers of formula I is substantially less soluble than the 1S cis S-/1R cis R-enantiomer pair.

In the process of the invention, as the 1:1 mixture of the 1R cis S- and 1S cis R-isomers crystallises out from the solution of cis-isomers, the solution tends to become relatively depleted in 1R cis S- and 1S cis R-isomers. This tendency is counter-balanced by the effect of the organic amine base in causing the mixture of cis-isomers to tend to become a racemic mixture of all four cis-isomers. Thus as the 1:1 mixture of 1R cis S- and 1S cis R-isomers is removed from solution by crystallisation further of the 1R cis S- and 1S cis R-isomers are formed by racemisation.

If this process were allowed to continue, a final equilibrium would be attained between crystallised 1:1 mixture of 1R cis S- and 1S cis R-isomers and a solution saturated with 1R cis S- and 1S cis R-isomers and containing equivalent amounts of 1S cis S- and 1R cis R-isomers. Such a final equilibrium, or its attainment, is upset in the process of the invention by the removal by evaporation of the organic amine base. The evaporation causes the remaining solution to become more concentrated, and the combined crystillisation/racemisation discussed above continues until all the organic amine base has evaporated off.

As will be readily appreciated by those skilled in the art, the precise isomer constitution of the product of the process will be dependent on the balance between the rate of crystallisation, the rate of racemisation and the rate of evaporation. All of these rates will vary according to temperature. The rate of evaporation will also vary according to pressure.

When the starting material is partly or wholly crystalline, in order to ensure complete dissolution of the 1S cis S- and 1R cis R-isomers of the compound of formula I, it is preferred to dissolve the mixture of isomers of formula I in the organic amine base at elevated temperature, e.g. a temperature in the range 50° to 80° C., conveniently 60° to 70° C. If desired the resulting solution may be filtered in order to ensure the absence of any solid particles in the solution prior to crystallisation. However, when the starting material is in the form of an oil, e.g., in the case of a freshly prepared racemic mixture of cis-isomers, the mixture of isomers of formula I is advantageously dissolved in the organic amine base at ambient temperature.

Crystallisation may advantageously be effected at ambient temperature or below, and, where elevated temperatures have been employed in order to bring the mixture of cis-isomers into solution in the organic amine base, crystallisation is preferably effected by cooling the solution to ambient temperature or below.

The optimum temperatures for crystallisation and evaporation will in general be in the range 0° to 20° C. Conveneintly, crystallisation is initiated by seeding with a few crystals of 1:1 mixture of the 1R cis S- and 1S cis R-isomers of the compound of formula I.

Those skilled in the art will appreciate that the organic amine base which is evaporated off may readily be condensed and collected in known manner for re-use.

The product of the process of the invention will always contain more than 50% by weight of the 1R cis S- and 1S cis R-isomers, and provided that the rate of evaporation of the organic amine base is kept sufficiently slow, and that the initial mixture of cis-isomers was optically inactive the product may consist substantially entirely of a 1:1 mixture of 1R cis S- and 1S cis R-isomers of the compound of formula I.

The preferred organic amine bases contain six carbon atoms. Triethylamine and diisopropylamine have been found to be very effective organic amine bases. Of these, triethylamine is particularly preferred.

Although the presence of small amounts of water in the organic amine base may be tolerated, the amount of water should be less than 2% by weight of the base, advantageously less than 1%, more advantageously less than 0.5%, and the dissolution, crystallisation and evaporation are preferably carried out under substantially anhydrous conditions.

It will be appreciated that the most readily available starting material for the process of the invention will be a racemic mixture of all four cis-isomers of the compound of formula I, although the process is equally applicable to starting materials containing non-racemic mixtures of cis-isomers.

The product of the process of the invention contains a high proportion of the most pesticidally-active isomer of the relevant compound of formula I. The invention also extends therefore to a mixture of cis-isomers of a compound of formula I consisting predominantly of the 1R cis S- and 1S cis R-isomers whenever prepared by the process of the invention, to a pesticidal composition comprising the said mixture in association with a suitable carrier therefor, and to a method of combating pests at a locus which comprises applying to the locus an effective amount of the said mixture or a composition containing the said mixture. The constitution of suitable pesticidal compositions is described in the aforementioned U.K. Pat. No. 1,413,491.

The invention will be further understood from the following Examples, of which Examples 1 and 2 relates to an embodiment of the process of the invention and Examples 3 and 4 relate to tests indicative of the suitability of organic amine systems for use in the process of the invention. Examples 1 to 3 were carried out under substantially anhydrous conditions, the water content of the triethylamine being 0.1% w/w.

EXAMPLE 1

10 g of a mixture of cis-isomers of α-cyano-3-phenoxybenzyl 3-(2,2-dichlorovinyl)-2,2-dimethylcyclopropanecarboxylate, in which the by weight ratio of 1S cis S- and 1R cis R isomers to 1R cis S- and 1S cis R-isomers was 2:1, was dissolved in 20 ml of triethylamine with heating to 60° to 70° C. The solution was allowed to cool to ambient temperature, with stirring, and was seeded with a few crystals of a 1:1 mixture of 1R cis S- and 1S cis R-isomers of α-cyano-3-phenoxybenzyl 3-(2,2-dichlorovinyl)-2,2-dimethyl-cyclopropane carboxylate. Stirring was continued for 40 hours at ambient temperature and the triethylamine was then stripped off at 20° C. over a period of one hour to leave 10 g of dry solid material, mp 65°–77° C., which was shown by gas-liquid chromatography to be a 98.9% pure mixture of cis-isomers of α-cyano-3-phenoxybenzyl 3-(2,2-dichlorovinyl)-2,2-dimethylcyclopropane carboxylate and by high performance liquid chromatography to contain 20 parts by weight of the 1S cis S- and 1R cis R-isomers and 80 parts by weight of the 1R cis S- and 1S cis R-isomers.

EXAMPLE 2

15 g of a mixture of cis-isomers of α-cyano-3-phenoxybenzyl 3-(2,2-dichlorovinyl)-2,2-dimethylcyclopropanecarboxylate, in which the by weight ratio of 1S cis S- and 1R cis R-isomers to 1R cis S- and 1S cis R-isomers was 1:1, was dissolved in 30 ml of triethylamine with heating to 60° to 70° C. The solution was allowed to cool at ambient temperature, with stirring, and was seeded with a few crystals of a 1:1 mixture of 1R cis S- and 1S cis R-isomers of α-cyano-3-phenoxybenzyl 3-(2,2-dichlorovinyl)-2,2-dimethylcyclopropanecarboxylate. After stirring for a further 42 hours at ambient temperature, a slow stream of nitrogen was bubbled through the solution in order to evaporate off the triethylamine. The solid residue, which was substantially dry after 24 hours, was transferred to a round-bottomed flask, washing with 20 ml of 60/80 petroleum ether. Evaporation to dryness at 50° C. yielded 14.85 g of dry solid material, mp 78°–81° C., which was shown by high performance liquid chromatography to contain greater than 90% by weight of a 1:1 mixture of the 1R cis S- and 1S cis R-isomers of α-cyano-3-phenoxybenzyl 3-(2,2-dichlorovinyl)-2,2-dimethylcyclopropanecarboxylate.

EXAMPLE 3

For comparison purposes several different organic amines were used as base-solvent systems in the following test procedure. 5.0 g of a mixture of cis-isomers of α-cyano-3-phenoxybenzyl 3-(2,2-dichlorovinyl)-2,2-dimethylcyclopropane carboxylate, in which by weight ratio of 1S cis S- and 1R cis R-isomers to 1R cis S- and 1S cis R-isomers was 2:1, was dissolved in 10 ml of the organic amine with heating (to not more than 60° C.). The resulting solution was allowed to cool to ambient temperature with stirring, was seeded with a few crystals of a 1:1 mixture of 1R cis S- and 1S cis R-isomers of α-cyano-3-phenoxybenzyl 3-(2,2-dichlorovinyl)-2,2-dimethylcyclopropane carboxylate. Stirring was continued overnight and the solution was then subjected to further treatment, analysis, etc. as appropriate. Results are given in Table I following. Analyses of solutions and end products were effected by high performance liquid chromatography. In cases where crystallisation did not occur at ambient temperature the solutions were cooled to −10° C. in order to attempt to achieve crystallisation.

TABLE I

| Test No. | Organic Amine | Comments |
|---|---|---|
| i | triethylamine | Slow crystallisation. After two days of stirring, precipitate was filtered and dried to give 2.0 g of 98% pure 1:1 mixture of 1R cis S- and 1S cis R isomers. Filtrate contained substantially racemic mixture of cis - isomers. No decomposition of starting material detectable. |
| ii | diisopropylamine | Slow crystallisation. After two days of stirring, precipitate was filtered and dried to give 2.0 g of a 98% pure 1:1 mixture of 1R cis S- and 1S cis R- isomers. Filtrate contained substantially racemic mixture of cis - isomers. About 5% decomposition of starting material detected. |
| iii | tri-n-propylamine | Rapid crystallisation. After stirring over weekend, precipitate was filtered, washed with 60-80 petroleum ether and dried to give 3.3 g of crystalline material having substantially the same composition as the starting material. |
| iv | tri-n-butylamine | Slow crystallisation. After stirring over weekend, precipitate was filtered, washed with 60-80 petroleum ether and dried to give 3.9 g of crystalline material having substantially the same composition as the starting material. |
| v | diethylamine | No crystallisation. Stirred for two hours at −10° C., still no crystallisation. About 20% decomposition of starting material detected after one day. |
| vi | n-hexylamine | No crystallisation. Rapid decomposition of starting material had occurred. |
| vii | n-butylmethylamine | No crystallisation, even after five days. About 50% decomposition of starting material detected after one day. Over 90% decomposition detected after nine days. |
| viii | N—cyclohexylmethylamine | No crystallisation even after three days. About 50% decomposition of starting material detected after three days. |
| ix | N—cyclohexylisopropylamine | No crystallisation after three days. Very little decomposition of starting material. Solution contained substantially racemic mixture of cis - isomers. |
| x | ethyldiisopropylamine | Rapid crystallisation. After stirring over weekend precipitate was filtered and dried to give 3.0 g of crystalline material having substantially the same composition as the starting material |
| xi | N,N—dimethylaniline | No crystallisation. |
| xii | 2,6-lutidine | No crystallisation. No decomposition of starting material detected. Isomer composition of starting material unchanged. |

EXAMPLE 4

Experiments to assess the effect of the presence of water in the base-solvent system were effected by the procedure of Example 3. In each case the base-solvent was triethylamine. Results are given in Table II following.

TABLE II

| Test No. | % water in triethylamine (w/w) | Comments |
|---|---|---|
| i | 0.10 | see Table I |
| ii | 2 | Slow crystallisation. After two days of stirring, precipitate was filtered and dried to give 0.9 g of a 98% pure 1:1 mixture of 1R cis S- and 1S cis R- isomers Filtrate contained substantially racemic mixture of cis - isomers |
| iii | 5 | No crystallisation even after five days |

I claim:

1. A process for increasing the 1R cis S isomer content in a mixture of cis-isomers of a compound of formula:

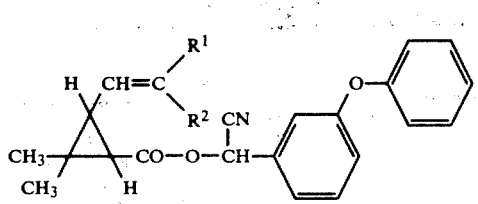

wherein R¹ and R² are independently chlorine, bromine or methyl, comprising the steps of:

dissolving as a solute a cis-isomer mixture of compound (I) which contains substantial quantities of 1R cis R-isomer and 1S cis S-isomer in an organic amine base having from 5 to 7 carbon atoms selected from a group consisting of secondary amines having two branched alkyl groups and tertiary amines;

evaporating the amine from said solute, whereby during evaporation the dissolved 1R cis R and 1S cis S-isomer content of said solute is progressively epimerized to 1R cis S and 1S cis R-isomers, respectively, which progressively crystallize from said solution as the amine content thereof diminishes by evaporation; and continuing evaporation until substantially all of said amine is removed from said solute, whereby said solute is recovered as a 1:1 crystalline mixture of 1R cis S and 1S cis R isomers.

2. A process according to claim 1, wherein R¹ and R² are both chlorine.

3. A process according to claim 1 wherein the organic amine base contains six carbon atoms.

4. A process according to claim 1 wherein dissolution in the organic amine base and crystallization from the resulting solution are effected under substantially anhydrous conditions.

5. A process according to claim 1, wherein evaporation of the organic amine base is effected at about 0° to about 20° C.

6. The process of claim 4, wherein water comprises less than about 0.5 percent by weight of the organic amine base.

7. The process of claim 1, wherein the mixture of 1S cis S-isomers and 1R cis R-isomers of the compound of formula I is dissolved in the organic amine base in the presence of 1R cis S-isomers and 1S cis R-isomers.

8. The process of claim 1, wherein the tertiary amine is triethylamine.

9. The process of claim 1, wherein the secondary amine having two branched alkyl groups is diisopropylamine.

10. The process of claim 1, wherein the mixture of isomers of the compound of formula I is dissolved in the organic amine base at an elevated temperature of about 50° to about 80° C.

11. The process of claim 1, wherein the solution of cis-isomers is maintained at about 0° to about 20° C. for about 40 hours with stirring followed by evaporation of the organic amine base.

* * * * *